(12) United States Patent  
Narciso-Martinez et al.

(10) Patent No.: US 9,770,579 B1  
(45) Date of Patent: Sep. 26, 2017

(54) PUSH-BUTTON OPERATED EPIDURAL CATHETER CONNECTOR

(71) Applicants: Luis Alberto Narciso-Martinez, Caracas (VE); Maura Spizzo De Narciso, Caracas (VE)

(72) Inventors: Luis Alberto Narciso-Martinez, Caracas (VE); Maura Spizzo De Narciso, Caracas (VE)

(*) Notice: Subject to any disclaimer, the term of this patent is extended or adjusted under 35 U.S.C. 154(b) by 366 days.

(21) Appl. No.: 14/734,182

(22) Filed: Jun. 9, 2015

(51) Int. Cl.
    *A61M 5/32* (2006.01)
    *A61M 39/10* (2006.01)
    *A61M 39/12* (2006.01)
    *A61M 39/02* (2006.01)

(52) U.S. Cl.
    CPC ........ *A61M 39/1011* (2013.01); *A61M 39/02* (2013.01); *A61M 39/12* (2013.01); *A61M 2039/0202* (2013.01); *A61M 2039/0205* (2013.01); *A61M 2039/1016* (2013.01); *A61M 2039/1027* (2013.01)

(58) Field of Classification Search
    CPC ............ A61M 2005/3132; A61M 5/32; A61M 2005/3268; A61M 2205/353
    See application file for complete search history.

(56) References Cited

U.S. PATENT DOCUMENTS

| | | | |
|---|---|---|---|
| 4,006,744 A | 2/1977 | Steer | |
| 4,405,163 A | 9/1983 | Voges et al. | |
| 4,792,163 A | 12/1988 | Kulle | |
| 4,929,236 A | 5/1990 | Sampson | |
| 5,368,573 A | 11/1994 | Andrew | |
| 5,464,400 A | 11/1995 | Collins | |
| 5,496,274 A | 3/1996 | Graves et al. | |
| 6,350,260 B1 | 2/2002 | Goebel et al. | |
| 7,044,936 B2 | 5/2006 | Harding et al. | |
| 7,717,900 B2 | 5/2010 | di Palma | |
| 8,142,417 B2 | 3/2012 | Pajunk et al. | |
| 8,480,560 B2 | 7/2013 | Vendely | |
| 8,647,300 B2 | 2/2014 | Kunzler et al. | |
| 8,696,647 B2 | 4/2014 | Bizup et al. | |
| 2012/0041426 A1 | 2/2012 | Bizup | |

*Primary Examiner* — Kevin C Sirmons  
*Assistant Examiner* — Deanna K Hall  
(74) *Attorney, Agent, or Firm* — H. John Rizvi; Gold & Rizvi, P.A.

(57) ABSTRACT

A catheter connector device for connecting a syringe or other fluid application and/or removal device, and a catheter is provided comprising a port for receiving a catheter, a port for connecting a syringe or other fluid application and/or removal device, and a push-button for securing the received catheter. The push-button includes internal arms embracing internal cantilevered structures in turn embracing a flexible tubular sleeve into which the catheter is inserted; when the push-button is pushed to an inward position, the arms of the push-button apply a pressure on the cantilevered structures, and thus on the tubular sleeve, gripping the catheter.

20 Claims, 7 Drawing Sheets

PUSH-BUTTON OPERATED EPIDURAL CATHETER CONNECTOR

FIELD OF THE INVENTION

The present invention relates generally to medical devices, and more particularly, to a push-button operated catheter connector device which can facilitate quick and easy connection of a syringe or other fluid application and/or removal device to an epidural catheter inserted into the epidural space of a patient and protruding outwardly from the patient's body.

BACKGROUND OF THE INVENTION

Catheters are thin tubes commonly used in medicine for accurately administering or withdrawing fluids. Typically, one end of a catheter is inserted into a patient, and an opposite end is connected to a fluid application and/or removal device, such as a syringe, for appropriately administering or withdrawing fluids to or from a patient. A catheter is usually connected to a syringe via an interfacing catheter connector. Such catheter connectors enable a medical practitioner to accurately administer or drain fluids by operating the connected syringe. However, traditional catheter connectors have various problems.

For example, traditional catheter connectors are commonly composed of a single part cone shaped or cylindrical tube, in which a catheter is inserted into one end of the tube, and a syringe, is attached at an opposite end of the tube. Such traditional catheter connectors usually rely solely on material tension of the connector tube to secure a catheter, and thus can result in an insecure connection.

Further, some common traditional catheter connectors require assembling and/or configuring multiple external parts to properly connect a catheter to a syringe. For example, some common catheter connectors require inconvenient latching, clamping and/or attaching various external components, such as plastic flaps, clamps, hinges, etc. Most catheter connectors are manufactured to be cheap and space-efficient. As such, these external parts may easily break, or may be hard to operate in emergency situations.

Epidural catheter connectors are a specific type of catheter connector designed to interface between a fluid application and/or removal device and an epidural catheter inserted into the epidural space and protruding from the patient's body, generally for providing controlled and extremely precise administration of epidural anesthetics. An epidural catheter must tightly yet unobtrusively grip the catheter in order to prevent disconnection of the catheter (which can be harmful to the patient) and guarantee correct flow of the epidural anesthetic through the catheter. In addition, epidural catheter connectors should preferably be easy to attach to the catheter, minimizing the risk of errors and pulling of the catheter. Epidural catheter connectors known in the art, namely, catheter-clamping connectors and threaded connectors are in risk of obstructing the catheter and also require excessive manual operation of the connector in order to fasten onto the catheter.

Thus, there is an established need for an epidural catheter connector device that can easily and safely be attached to an epidural catheter in order to facilitate the further connection of a syringe or other fluid application and/or removal device to a catheter for delivery of medical fluids to or remove fluids from a patient.

SUMMARY OF THE INVENTION

This summary is provided to introduce a selection of concepts in a simplified form that are further described below in the detailed description. This summary is not intended to identify key features of essential features of the claimed subject matter, nor is it intended to be used to limit the scope of the claimed subject matter. Furthermore, the claimed subject matter is not limited to implementations that solve any or all disadvantages noted in any part of this disclosure.

According to embodiments of the present disclosure, a catheter connector device for interfacing between a catheter and a syringe is disclosed. The catheter connector device includes a first port for attaching a syringe or other fluid application and/or removal device, and a second port for inserting a catheter or thin tube. The catheter connector device further includes a finger-operable push-button which can be pressed inward, towards the cavity. When the push-button is in a rest position, a catheter can be inserted freely into the tubular sleeve via the port hole. When the push-button is pushed toward the cavity, two arms of the push-button impose a force on cantilevered structures and an underlying flexible tubular sleeve disposed inside the cavity, securing the inserted catheter. When secured, liquid can flow from an attached syringe through the catheter without leakage.

Introducing a first embodiment of the invention, the invention consists of a catheter connector device for interfacing between a catheter and a fluid application and/or removal device, the catheter connector device comprising a catheter connector main body delimiting an internal cavity. A first port and a second port are formed on the catheter connector main body. The first and second ports include respective first and second holes communicating the internal cavity with an outside of the catheter connector main body At least two flexible cantilevered structures extend from the catheter connector main body into the internal cavity. A flexible tubular sleeve is arranged between the at least two cantilevered structures. The flexible sleeve includes a longitudinal through hole in fluid communication with the first and second holes. The catheter connector device further includes a push-button, comprising a push-button body operable from outside the catheter connector main body, and at least two arms extending into the internal cavity. The arms are arranged in a spaced-apart configuration, wherein first portions of the arms are separated a first distance. The catheter connector device is configured to adopt a non-gripping position and a non-gripping position relative to the catheter connector main body. In the non-gripping position, the cantilevered arms are biased to separate from one another and occupy a width that is greater than the first distance. In the gripping position, the push-button is pushed inwardly towards the internal cavity, and the first portions of the arms embrace and retain the cantilevered structures in a deformed position; in this deformed position, the cantilevered structures apply a pressure against the flexible tubular sleeve and compress the flexible sleeve for gripping a catheter inserted in the longitudinal through hole of the flexible tubular sleeve.

In a second aspect, the arms of the push-button can further include respective second portions separated an increasing distance greater than the first distance, the second portions extending from the first portions oppositely to the push-button body. Transition from the non-gripping position to the gripping position can be caused by the second portions of the arms moving transversely upon and frictioning against the cantilevered structures and pushing the cantilevered structures towards one another.

In another aspect, the second portion of each arm is tapered.

In another aspect, the arms of the push-button can also include respective third portions separated a second distance greater than the first distance. When the catheter connector device is in the non-gripping position, the third portions can embrace the cantilevered arms.

In another aspect, one or more of the at least two arms can include a lip configured to engage with a mating lip of the catheter connector main body when the catheter connector device is in the gripping position, preventing the push-button from moving outwardly from the gripping position to the non-gripping position.

In another aspect, the first port and the second port can be arranged at opposite ends along a longitudinal direction of the catheter connector main body. The first hole, the tubular sleeve and the second hole can be aligned along the longitudinal direction.

In another aspect, the push-button can further include at least one limiting lip engageable with an internal surface of the catheter connector main body and preventing the push-button from being removed from the main body.

In another aspect, the catheter connector main body can be formed of a first body portion and a second body portion fastened to one another. The first port can be comprised in the first body portion, and the second port can be comprised in the second body portion.

In another aspect, the internal cavity can be enclosed by an end wall of the first body portion, the end wall comprising the first port, and by at least one sidewall of the first body portion. The second body portion can be arranged at an end of the at least one sidewall opposite to the end wall.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the claimed subject matter will hereinafter be described in conjunction with the appended drawings provided to illustrate and not to limit the scope of the claimed subject matter, where like designations denote like elements, and in which:

It is to be understood that like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
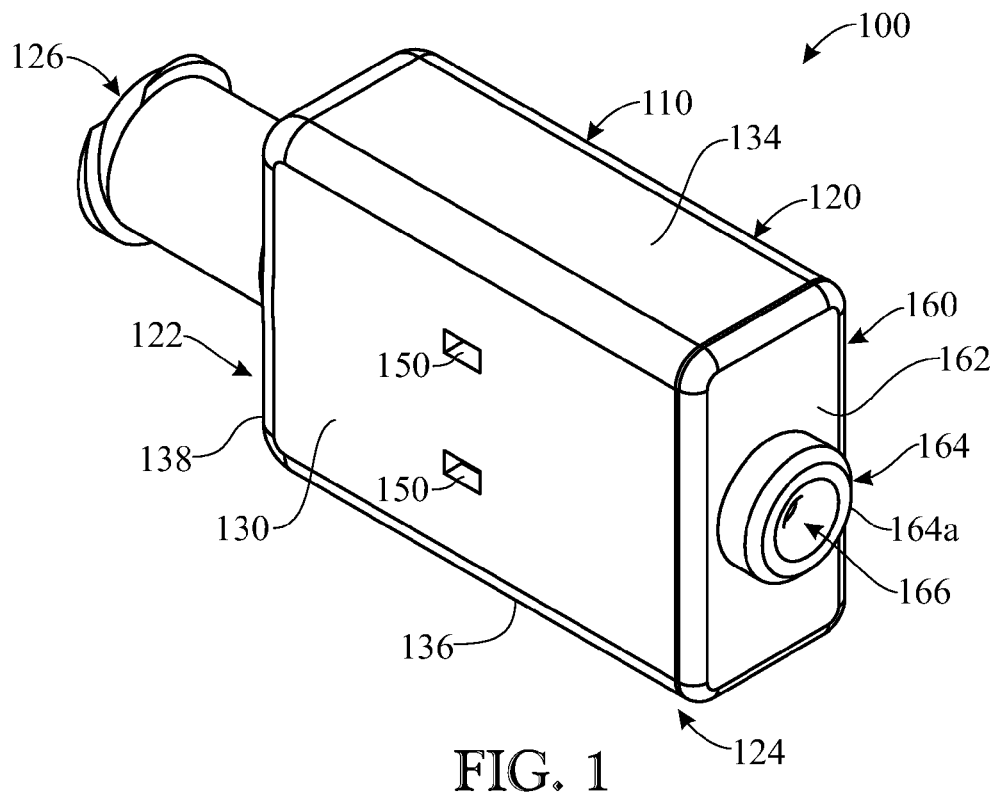
FIG. 1 presents an isometric front view of a catheter connector device in accordance with a first exemplary embodiment of the invention.
Figure 2:
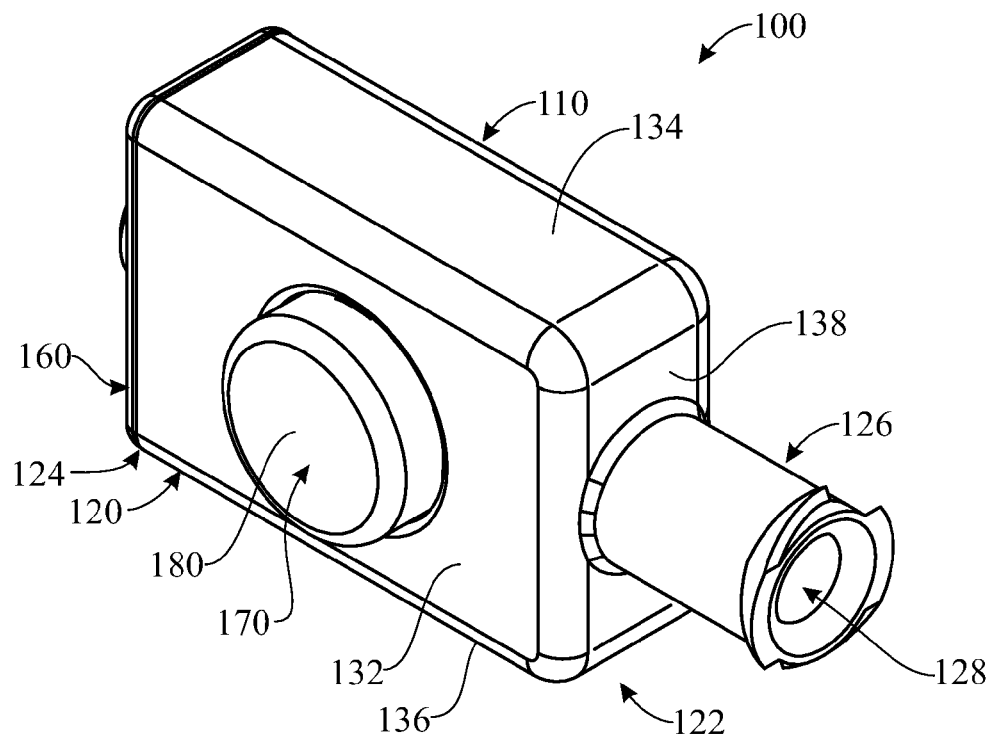
FIG. 2 presents an isometric rear view of the catheter connector device of FIG. 1.
Figure 3:
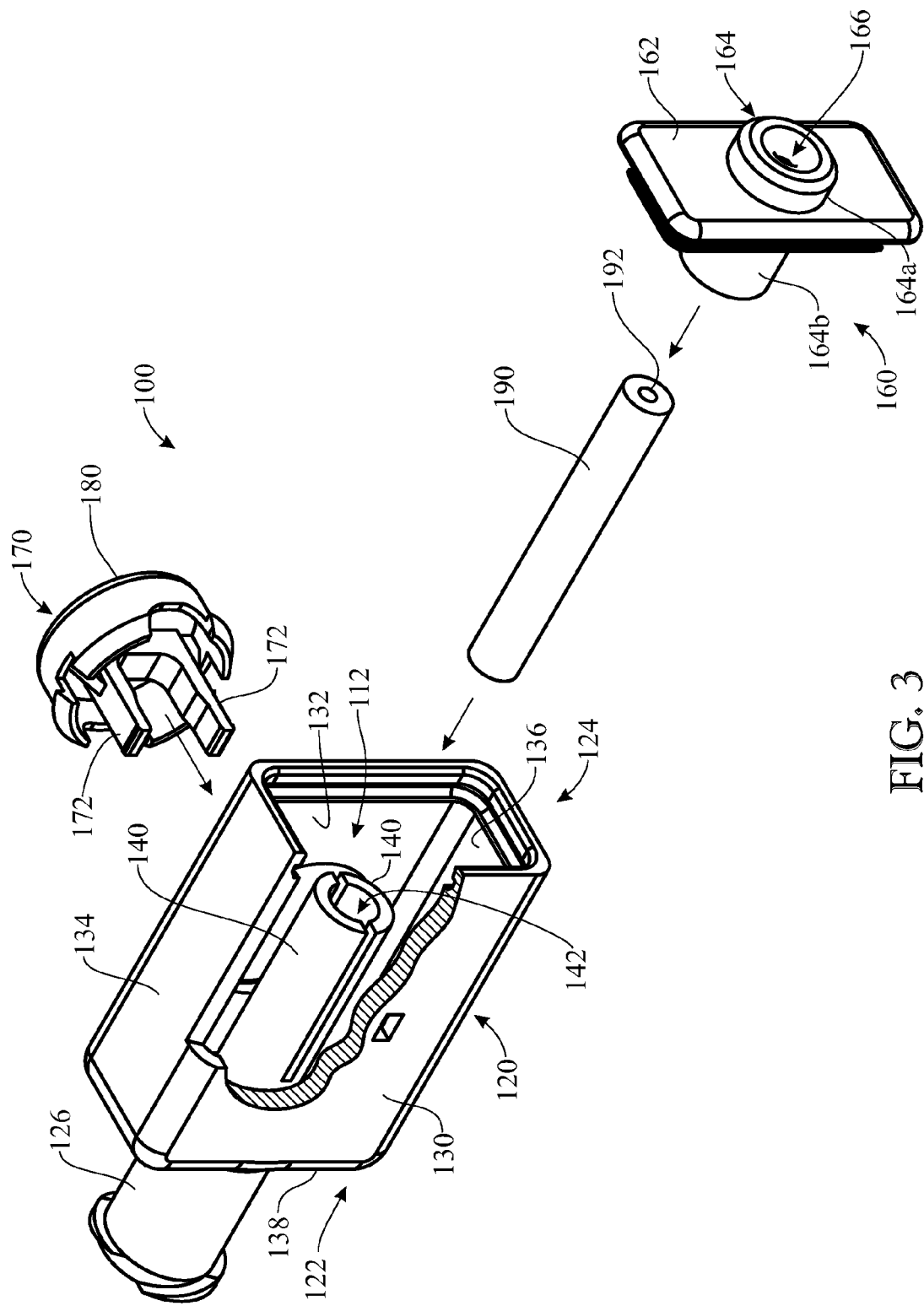
FIG. 3 presents an isometric front exploded view of the catheter connector device of FIG. 1.
Figure 4:
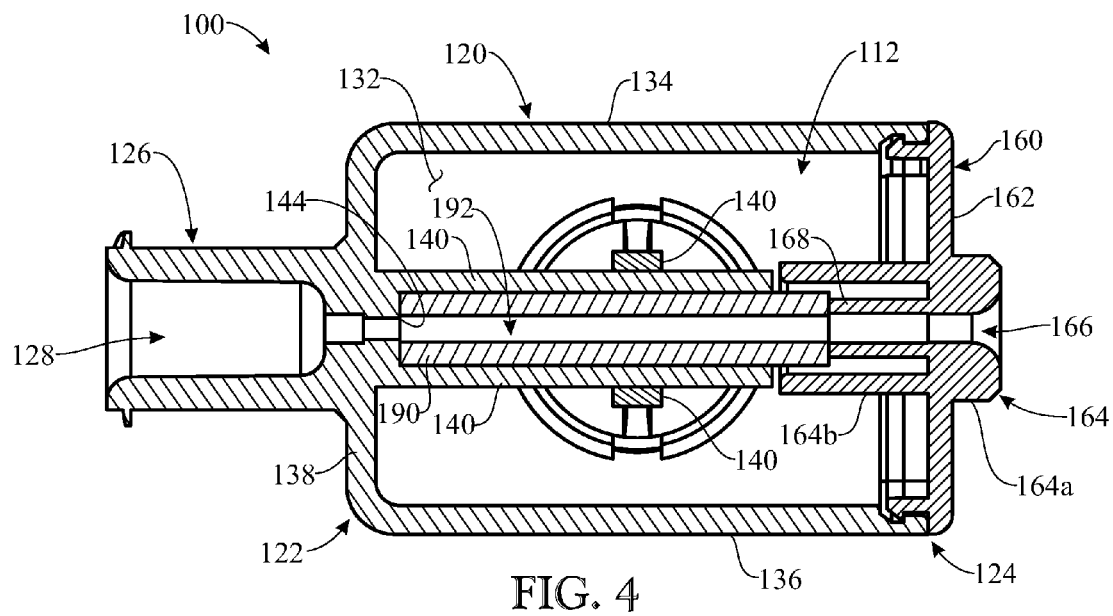
FIG. 4 presents a cross-sectional side elevation view of the catheter connector device of FIG. 1.
Figure 5:
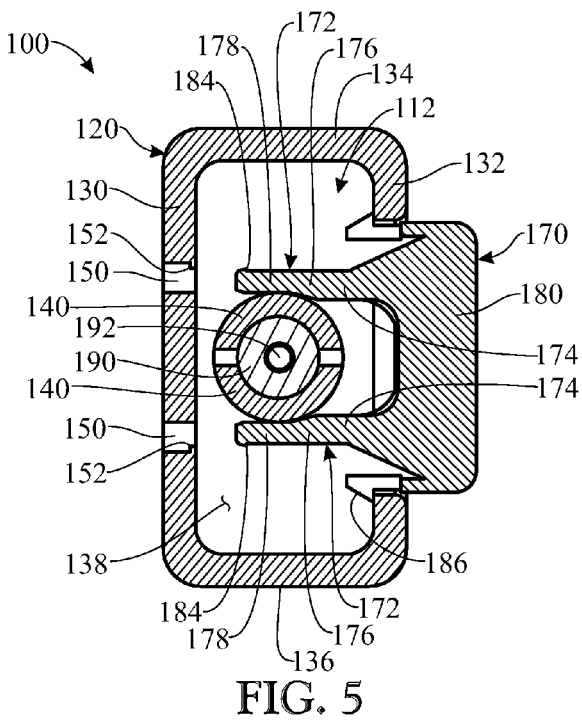
FIG. 5 presents a cross-sectional front elevation view of the catheter connector device of FIG. 1.

The illustrations of FIGS. 1 through 9 show a catheter connector device 100 in accordance with a first embodiment of the present invention. The illustration of FIG. 1 shows the catheter connector device 100 including a hollow catheter connector main body 110 having an internal cavity 112 (FIGS. 3-5). The catheter connector main body 110 of the present embodiment is formed of a first body portion 120 and a second body portion 160 which are attached to one another to form the catheter connector main body 110 and enclose the internal cavity 112. The catheter connector main body 110 may be composed of any appropriate material, such as plastic or a composite, or combinations thereof. The first body portion 120 and second body portion 160 may be composed of same or different materials.

Figure 6:
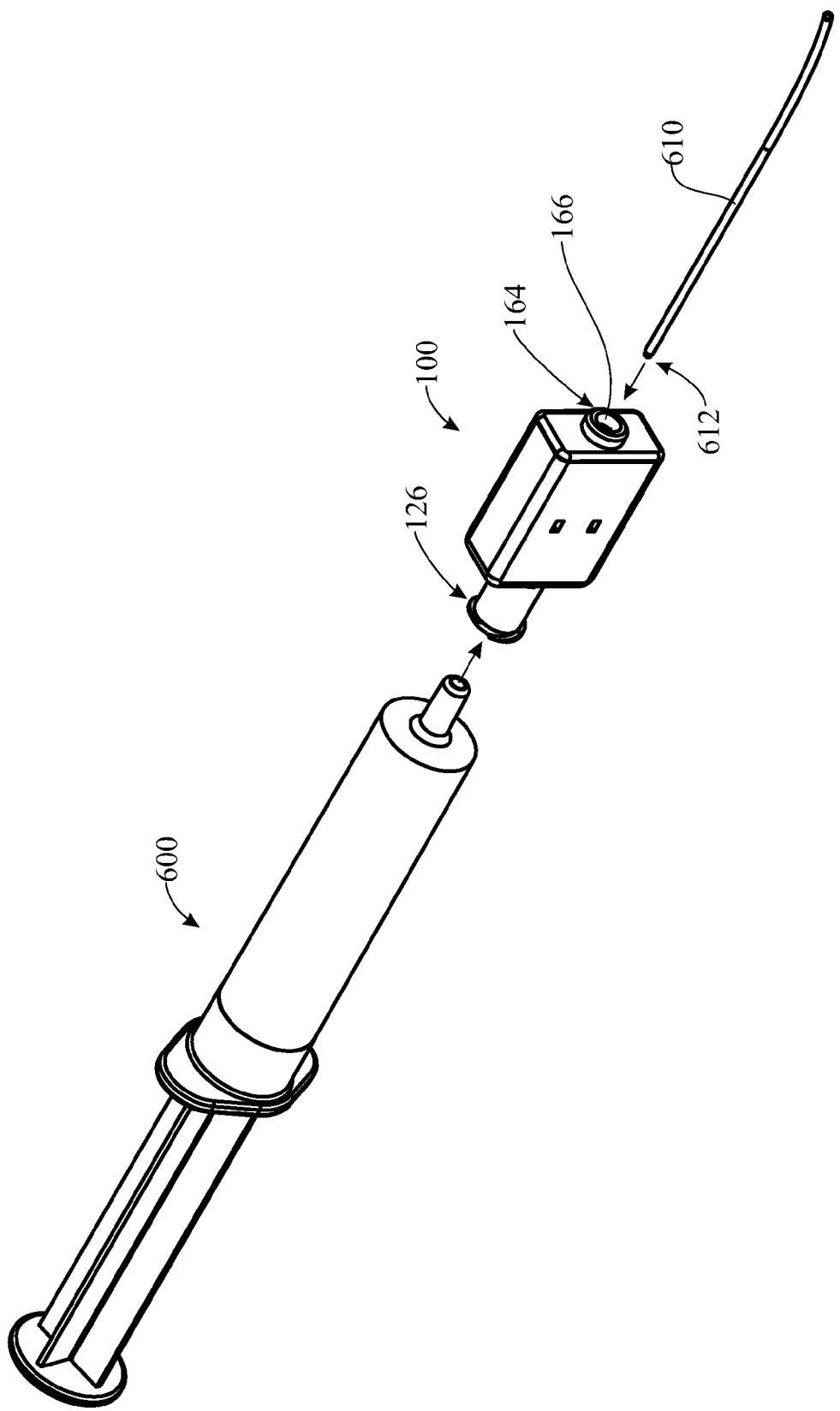
FIG. 6 presents an isometric front view of the catheter connector device of FIG. 1, a syringe, and a catheter, shown exploded.
Figure 7:
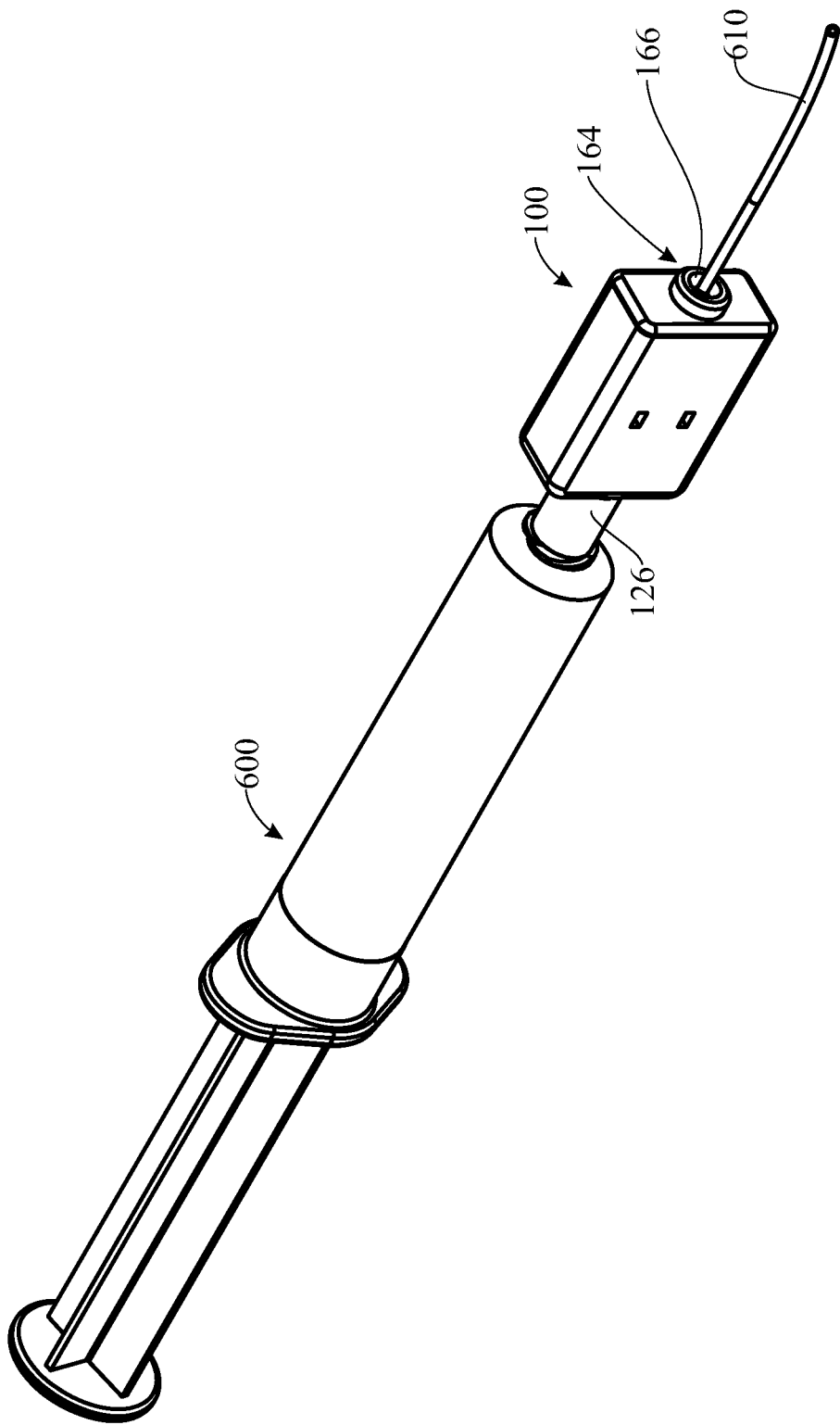
FIG. 7 presents an isometric front view of the catheter connector device, syringe, and catheter of FIG. 6, shown assembled.

The first body portion 120 includes a first end 122 and a second end 124, such that the second end 124 is the opposite first end 122 along a longitudinal direction of the catheter connector main body 110. As can be seen in FIGS. 1 and 2, the first body portion 120 includes a first port 126 at first end 122 for connecting a syringe or other fluid application and/or removal device. For example, FIGS. 6 and 7 show a syringe 600 being attached to first port 126. It is to be understood that for description purposes, this disclosure refers to a syringe as an example of a fluid application and/or removal device. In other words, any appropriate fluid application and/or removal device may be used in place of a syringe to apply or withdraw fluids. Turning to FIG. 2, the first port 126 includes a first port hole 128. The syringe 600 can be attached to first port 126 via any means such that a vacuum seal is formed at an interface of syringe 600 and first port 126. Upon operation of the syringe 600, liquid is able to flow in and out of first port hole 128. For example, the syringe 600 may be attached via a screw mechanism, a snap-lock mechanism, or the like. Such a vacuum seal may be accomplished via a rubber O-ring, or the like, disposed at first port hole 128, such that liquid may flow bi-directionally between the syringe 600 and the first port hole 128.

In addition, as can be seen in FIGS. 1-4 and especially in FIG. 5, the first body portion 120 includes a first side wall 130, an opposing second side wall 132, a top wall 134, a bottom wall 136 and a first end wall 138. The first side wall 130, second side wall 132, top wall 134 and bottom wall 136 extend from the first end wall 138 to the second end 124 of the first body portion 120. The walls 130, 132, 134, 136 and the second body portion 160 delimit the internal cavity 112. The walls 130, 132, 134, 136 may take any shape, concavity or convexity while remaining within scope of this disclosure. For example, the first body portion 120 of the present embodiment has a substantially rectangular box or prism shape, where the walls 130, 132, 134, 136 are generally rectangular in shape.

As illustrated in FIG. 3, the first body portion 120 further includes two cantilevered structures 140 disposed inside the internal cavity 112. The cantilevered structures 140 are affixed to the first end wall 138 at the first end 122, and extend longitudinally toward the second end 124. The cantilevered structures 140 are flexible and can bend away from an initial position when subjected to a force. If such a force is removed, the cantilevered structures 140 relax to the initial position. The cantilevered structures 140 present inner concave surfaces in order for a tubular space 142 to be formed between the cantilevered structures 140. The tubular space 142 is in fluid communication with the first port hole 128 of the first port 126. The cantilevered structures 140 may take form as a single tube, or a plurality of structures to form tubular space 142. The cantilevered structures 140 may be composed of rubber, plastic and/or a composite. In the present embodiment, the cantilevered structures 140 are integrally formed with the rest of the first body portion 120 such as by plastic injection molding. The cantilevered structures 140 may be attached at one or more various points of first body portion 120.

The second body portion 160, in turn, is removably attachable to second end 124 of the first body portion 120, substantially enclosing the internal cavity 112. The second body portion 160 may be attached in any appropriate way, such as via hinges, rubber lining, magnetic components, or snap-lock structures for convenient attaching. The second body portion 160 includes a generally planar body 162 and a second port 164. The second port 164 can include an external portion 164*a* and an internal portion 164*b*, protruding from opposite external and internal surfaces of the generally planar body 162, as best shown in FIGS. 3 and 4. A second port hole 166 extends through the second port 164 and is configured to receive a catheter. Similar to the first port 126, the second port 164 may include various vacuum sealing devices or parts such as an O-ring or the like. Further, the second port 164 may include various components to aid in securing a catheter. For example, the second port 164 may include various teeth or frictional devices to increase a securing force or friction on the catheter. The second body portion 160 may be composed of any appropriate material, such as plastic, rubber or a composite, and may take any shape. For example, FIGS. 1-9 show the second body portion 160 having a substantially rectangular shape to match second end 124 of the first body portion 120.

As illustrated in FIGS. 2 and 3, the catheter connector device 100 further includes a push-button 170. The push-button 170 is movably coupled to the second side wall 132 of the first body portion 120, and includes two arms 172 and a push-button body 180 from which the two arms 172 extend inward and into the internal cavity 112, as further shown in FIGS. 5, 8, and 9. The push-button 170, and particularly the push-button body 180, may be shaped in any way without departing from the scope of this disclosure; as way of example, the push-button body 180 of the present embodiment is circular. The push-button 170 may include various components to guide, assist and/or appropriately limit movement. For example, the push-button 170 may include one or more a movement limiters to limit movement in a direction away from the internal cavity 112. For example, FIG. 5 shows push-button 170 including movement limiting lips 186 that appropriately stop push-button 170 from moving away from the internal cavity 112 at an appropriate distance, but allow the push-button 170 to be pushed inward towards the internal cavity 112. Such an appropriate distance may be chosen to allow comfortable tactile function for an operator pushing push-button 170. The limiting lips 186 may also serve to secure push-button 170 from falling out of first body portion 120, especially if push-button 170 is biased toward the rest position.

The arms 172 are spaced apart and configured to embrace the cantilevered structures 140. The distance between the arms 172 is non-constant, the distance being greater between the free ends of the arms 172 than between opposite ends of the arms 172 closer to the push-button body 180, in order for the arms 172 to apply an increasing force on the cantilevered structures 140 when the push-button 170 is pushed toward the internal cavity 112. In the present embodiment, as shown in FIG. 5, the arms 172 specifically include a first portion 174, a tapered second portion 176, and a third portion 178. The distance between the first portions 174 is less than the distance between the third portions 178. The tapered second portions 176, in turn, are separated by an increasing distance. It is to be understood that the push-button 170 and arms 172 may be configured in various ways. For example, the arms 172 may include sloped or concave portions for gripping the cantilevered structures 140. A width and/or thickness of arms 172 may take any value, and may be proportional to a length of cantilevered structures 140 such that an appropriate width and/or thickness may be chosen to deliver an appropriate force. A width of arms 172 may also be chosen to provide a desired structural modulus, tension, stiffness, or the like.

The illustrations of FIG. 1 shows two arm docks 150 disposed on the first side wall 130. The arm docks 150 of the present embodiment are shaped as two separate rectangular apertures passing through the first side wall 130. The push-button 170 and arms 172 may be configured such that the arms 172 and arm docks 150 meet when push-button 170 is substantially pushed toward the internal cavity 112, and so that the arm docks 150 and arms 172 lock upon meeting. The arms 172 and arm docks 150 may be configured in various ways for locking. For example, the arms 172 and arm docks 150 may each include lips 184, 152 that interlock upon meeting. However, any locking mechanism may be used to lock arms 172 to the first body portion 120 when the push-button 170 is in an inward position (FIG. 9). Once locked, it is preferable that the push-button 170 is not easily brought back to the rest position (FIGS. 5 and 8); for this purpose, the engagement of the lips 184, 152 takes place within the first side wall 130 and thus protected from disengagement. The arm docks 150 of the present embodiment are only slightly wider than the free ends of the arms 172, preventing inadvertent lateral movement of the arms 172 within the arm docks 150 and thus disengagement of the lips 184, 152.

The catheter connector device 100 further includes a flexible tubular sleeve 190, as illustrated in FIGS. 3-5, 8 and 9. As best shown in FIG. 4, the tubular sleeve 190 is disposed mainly in the tubular space 142 between the cantilevered structures 140, sandwiched by the inner concave surfaces of the cantilevered structures 140; preferably, the inner concave surfaces and the tubular sleeve 190 match in shape and size. An end portion of the tubular sleeve 190 is arranged inside the internal portion 164b of the second port 164, and resting on an internal neck 168 of the second port 164, the tubular sleeve 190 therefore being secured by the cantilevered structures 140 and the internal portion 164b. The tubular sleeve 190 includes a longitudinal through hole 192 which is generally aligned with the first port hole 128 and the second port hole 166 when the second body portion 160 is attached to the first body portion 120; the longitudinal through hole 192 is configured to receive a catheter. It is to be understood that the tubular sleeve 190 may be composed of any appropriate material, such as plastic, rubber, a composite, combinations thereof, or the like. The tubular sleeve 190 can deform when cantilevered structures are subjected to a force.

The catheter connector device 100 of the present embodiment is typically used for attaching to an epidural catheter and providing a port for a syringe 600 or other fluid application and/or removal device in order to apply epidural anesthetic through the epidural catheter. In typical operation, an anesthesiologist will have previously inserted a catheter 610 into the epidural space of a body of a patient, and a free end 612 of the catheter 610 shall protrude from the patient's body.

The anesthesiologist then removes a catheter connector device 100 from a sterilized packaging. The catheter connector device 100 is initially in the situation of FIG. 5, in which the push-button 170 is in an outer position but retained by the limiting lips 186 resting against an inner surface of the second side wall 132. The cantilevered structures 140 are embraced by the third portions 178 of the arms 172, and embrace the flexible tubular sleeve 190. In this initial position, the cantilevered structures 140 and flexible tubular sleeve 190 are preferably relaxed and not deformed.

The anesthesiologist then proceeds to insert the free end 612 of the catheter 610 into the second port 164 and through the second port hole 166, as demonstrated in FIG. 6. The catheter 610 is softly pushed into the catheter connector device 100, through the second port hole 166 and longitudinal through hole 192, deeply enough to overcome the cantilevered structures 140, thus achieving a first position, shown in cross-section in FIG. 8. For instance, the catheter 610 can be inserted until the free end 612 contacts respective end surfaces 144 of the cantilevered structures 140 and is longitudinally stopped by the end surfaces 144. As can be observed, in this first position the arms 172 subject an initial force on the cantilevered structures 140; this initial force can be relatively small or zero, and can cause little or no deformation of the cantilevered structures 140 towards one another, and little or no deformation of the flexible tubular sleeve 190 by the cantilevered structures 140. In this initial position, the catheter 610 may slide in and out of the longitudinal through hole 192 of the tubular sleeve 190, allowing the longitudinal position of the catheter 610 to be adjusted if needed.

Figure 8:
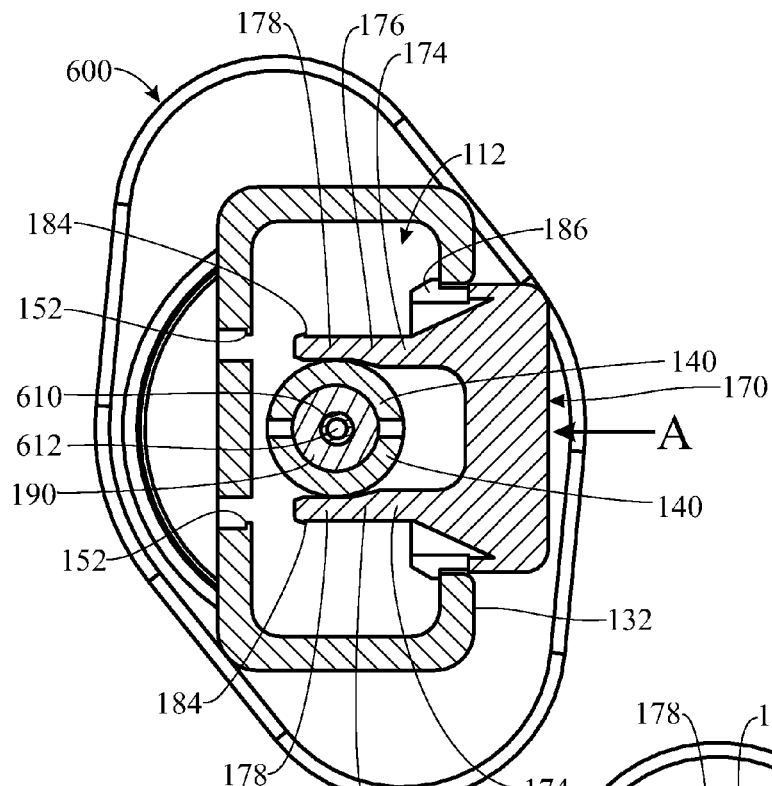
FIG. 8 presents a cross-sectional front elevation view of the catheter connector device and catheter of FIG. 7, wherein the catheter connector device is shown in a first position in which it does not substantially grip the catheter.
Figure 9:
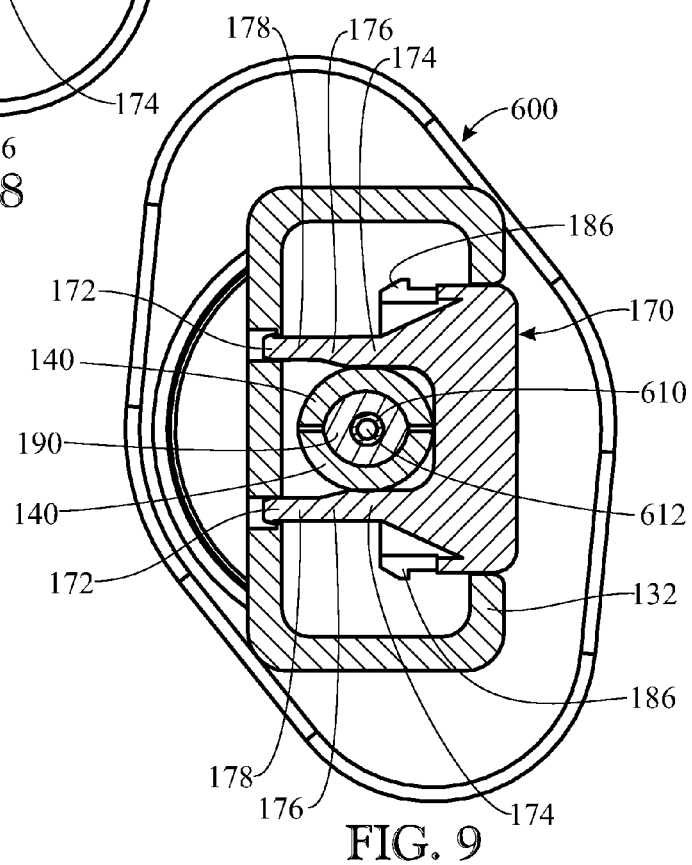
FIG. 9 presents a cross-sectional front elevation view of the catheter connector device, syringe, and catheter of FIG. 7, wherein the catheter connector device is shown in a second position in which it substantially grips the catheter, preventing it from being removed from the device, and the catheter connector device is ready for the syringe to apply a fluid therethrough.

Once the catheter 610 is appropriately inserted, the anesthesiologist simply pushes the push-button 170 inward as indicated by arrow A (FIG. 8). Inward pushing of the push-button 170 causes the arms 172 to move transversely over the cantilevered structures 140, while the cantilevered structures 140 remain substantially transversely static. Sufficient pressing of the push-button 170 causes the cantilevered structures 140, which were initially embraced by the third portions 178, to become contacted, and gradually pressed and pivoted inward by the tapered second portions 176 as the tapered second portions 176 move transversely over and against the cantilevered structures 140. Further inward pushing of the push-button 170 eventually causes the first portions 174, which are closer to one another than the third portions 178, to contact the cantilevered structures 140 and exert an inward force on the cantilevered structures 140 (a reaction force of the biasing force of the cantilevered structures 140 against the third portions 178), maintaining the cantilevered structures 140 in a pivoted position shown in FIG. 9 in which the cantilevered structures 140 are pivoted closer to one another. In this position, the deformed and tensioned cantilevered structures 140 press against the flexible tubular sleeve 190, thereby deforming the tubular sleeve 190 and causing the tubular sleeve 190 to apply a pressure on the catheter 610. The increased pressure—and thus increased friction—between the tubular sleeve 190 and catheter 610 is sufficiently high to prevent the catheter 610 from being pulled out of the tubular sleeve 190. From the point of view of the anesthesiologist, this sequence has simply required a pushing of the push-button until perceiving a clicking effect caused by the lips 184, 152 having engaged as the arms 172 meet arm docks 150.

In this final position, fluid communication is provided between the first port hole 128, longitudinal through hole 192 of the tubular sleeve 190, and the second port hole 166. Thus, the catheter connector device 100 enables liquid to flow from the first port 126 to the second port 164 and through catheter 610, via the first port hole 128, longitudinal through hole 192 of the tubular sleeve 190 and the second port hole 166, such that liquid does not leak into adjacent parts. In this final situation of FIG. 9, the syringe 600 may be attached to the first port 126 as described above. At this point, the syringe 600 can be operated to cause a liquid epidural anesthetic housed in the syringe 600 to flow through the first port hole 128 and the catheter 610 without leakage. As mentioned heretofore, it is to be understood that catheter 610 does not have to engage with first end 122 of first body portion 120 to be properly secured in accordance with this disclosure.

Alternative embodiments are contemplated in which the arms 172 may not be symmetrical, i.e. in which the first portions 174, tapered second portions 176, and third portions 178 may not be identical in both arms 172. In other embodiments, first portions 174, tapered second portions 176, and third portions 178 may be included on only one arm 172. Further, the push-button 170 may include more than two arms 172. Further, it is to be understood that arms 172 do not have to fully engage the arm docks 150 to properly secure catheter 610. In some cases the arm docks 150 may not be required to secure catheter 610; for example, arms 172 may provide enough force to secure catheter 610 as well as keep push-button 170 in place, or may even clip against alternative clipping surfaces of the catheter connector main body 110 or cantilevered structures 140.

Figure 10:
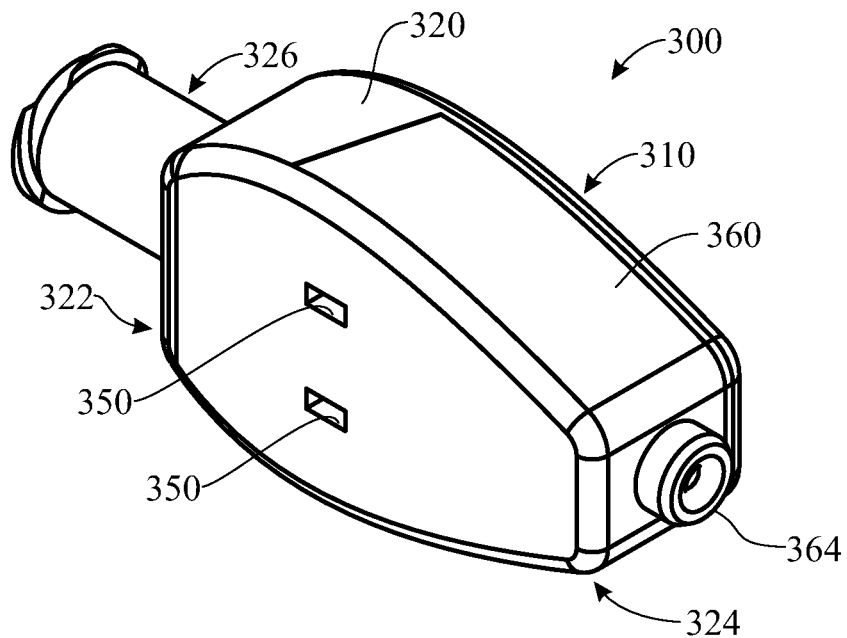
FIG. 10 presents an isometric front view of a catheter connector device in accordance with a second exemplary embodiment of the invention.
Figure 11:
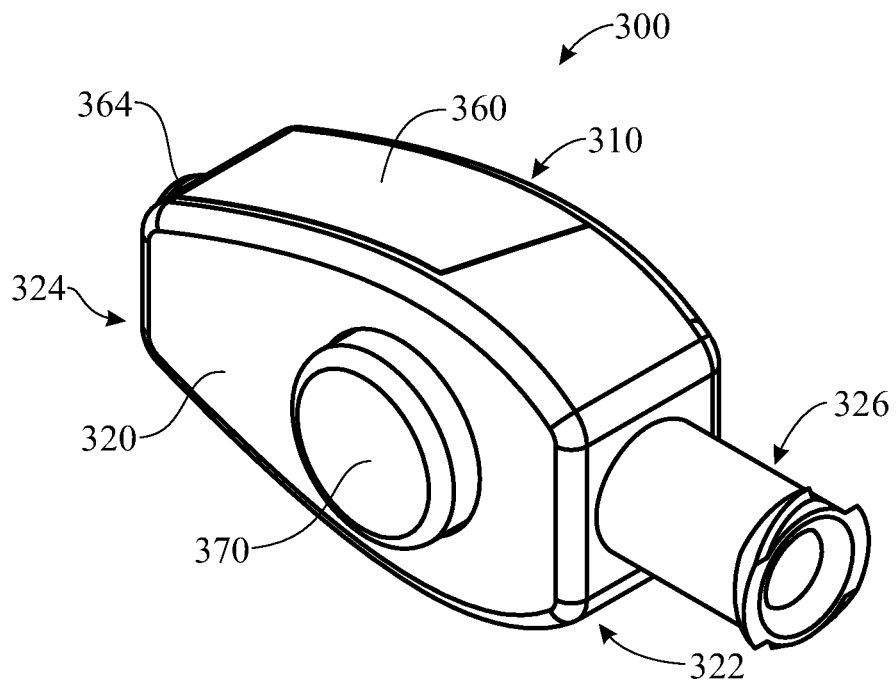
FIG. 11 presents an isometric rear view of the catheter connector device of FIG. 10.

The illustrations of FIGS. 10 and 11 show a further exemplary embodiment of a catheter connector device 300 in accordance with aspects of this disclosure. Like features of the catheter connector device 300 and the catheter connector device 100 (FIG. 1) are numbered the same except preceded by the numeral '3'. As shown in FIG. 10, the catheter connector device 300 including a catheter connector main body 310 having a first body portion 320 and a second body portion 360. The catheter connector device 300 may include the elements described with respect to the first embodiment above while having a different shape. For example, the first body portion 320 has a first end 322 and a second end 324 similarly disposed with respect to first end 122 and second end 124 of the embodiment described in FIGS. 1 through 9. The second body portion 360 is removably attached to the first body portion 320 at the second end 324, enclosing a cavity therein (not shown). The first body portion 320 has a non-rectangular, pear-like shape and the second body portion 360 is shaped to match the second end 324. The illustration of FIG. 10 further shows a first port 326, a second port 364 and arm docks 350 in accordance with the present disclosure. The illustration of FIG. 11 shows a push-button 370 in accordance with the present disclosure. It is to be understood that the exemplary embodiment shown in FIGS. 10 and 11 can include features described with respect to the first embodiment, but not shown in FIGS. 10 and 11. For example, first body portion 320 may form a cavity between two side walls, where one side wall has the push-button 370, which in turn may include the above described features of the first embodiment. As such, pushing the push-button 370 may lock a catheter in place such as catheter 610 as described above. Further, a syringe may be attached at the first port 326 as described above, such as syringe 600, for accurately administering or withdrawing fluids from or to the catheter.

In conclusion, provided is a catheter connector device that enables an operator to connect a syringe and a catheter by inserting the catheter at one end of the catheter connector device, attaching the syringe at another end of the catheter connector device, and simply pushing a push-button on the catheter connector device in order to secure the catheter to the catheter connector device.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A catheter connector device for interfacing between a catheter and a fluid application and/or removal device, the catheter connector device comprising:
   a catheter connector main body delimiting an internal cavity, wherein a first port and a second port are formed on the catheter connector main body, said first and second ports comprising respective first and second holes communicating said internal cavity with an outside of said catheter connector main body;
   at least two flexible cantilevered structures extending from said catheter connector main body into said internal cavity;
   a flexible tubular sleeve arranged between said at least two cantilevered structures, said flexible sleeve comprising a longitudinal through hole in fluid communication with said first and second holes;
   a push-button, comprising a push-button body operable from outside said catheter connector main body, and at least two arms extending into the internal cavity, said arms arranged in a spaced-apart configuration, wherein first portions of said arms are separated a first distance; wherein
   said catheter connector device is configured to adopt:
      a non-gripping position, in which said cantilevered structures are biased to separate from one another and occupy a width that is greater than said first distance, and
      a gripping position in which said push-button is pushed inwardly towards said internal cavity, and said first portions of said arms embrace and retain said cantilevered structures in a deformed position in which said cantilevered structures apply a pressure against said flexible tubular sleeve and compress said flexible sleeve for gripping a catheter inserted in said longitudinal through hole of said flexible tubular sleeve.

2. The catheter connector device of claim 1, wherein said arms of said push-button further comprise respective second portions separated an increasing distance greater than said first distance, said second portions extending from said first portions oppositely to said push-button body, wherein transition from said non-gripping position to said gripping position is causable by said second portions of said arms frictioning transversely against said cantilevered structures and pushing said cantilevered structures towards one another.

3. The catheter connector device of claim 2, wherein the second portion of each arm is tapered.

4. The catheter connector device of claim 2, wherein said arms of said push-button further comprise respective third portions separated a second distance greater than said first distance, wherein, when said catheter connector device is in said non-gripping position, said third portions embrace said cantilevered structures.

5. The catheter connector device of claim 1, wherein one or more of said at least two arms comprises a lip configured to engage with a mating lip of said catheter connector main body when said catheter connector device is in said gripping position, preventing said push-button from moving outwardly from said gripping position to said non-gripping position.

6. The catheter connector device of claim 1, wherein said first port and said second port are arranged at opposite ends along a longitudinal direction of said catheter connector main body, and wherein said first hole, said tubular sleeve and said second hole are aligned along said longitudinal direction.

7. The catheter connector device of claim 1, wherein said push-button further comprises at least one limiting lip engageable with an internal surface of said catheter connector main body and preventing said push-button from being removed from said main body.

8. The catheter connector device of claim 1, wherein said catheter connector main body is formed of a first body portion and a second body portion fastened to one another, where said first port is comprised in said first body portion and wherein said second port is comprised in said second body portion.

9. The catheter connector device of claim 8, wherein said internal cavity is enclosed by an end wall of said first body portion, said end wall comprising said first port, and by at least one sidewall of said first body portion, and wherein said second body portion is arranged at an end of said at least one sidewall opposite to said end wall.

10. A catheter connector device for interfacing between a catheter and a fluid application and/or removal device, the catheter connector device comprising:
   a catheter connector main body delimiting an internal cavity, wherein a first port and a second port are formed on the catheter connector main body, said first and second ports comprising respective first and second holes communicating said internal cavity with an outside of said catheter connector main body;
   at least two flexible cantilevered structures extending from said catheter connector main body into said internal cavity;
   a flexible tubular sleeve arranged between said at least two cantilevered structures, said flexible sleeve comprising a longitudinal through hole in fluid communication with said first and second holes;
   a push-button, comprising a push-button body operable from outside said catheter connector main body, and at least two arms extending into the internal cavity, said arms arranged in a spaced-apart configuration, wherein first portions of said arms are separated a first distance, and second portions of said arms are separated an increasing distance greater than said first distance; wherein
   said catheter connector device is configured to adopt:
      a non-gripping position, in which said cantilevered structures are biased to separate from one another and occupy a width that is greater than said first distance, and
      a gripping position in which said push-button is pushed inwardly towards said internal cavity, and said first portions of said arms embrace and retain said cantilevered structures in a deformed position in which said cantilevered structures apply a pressure against said flexible tubular sleeve and compress said flexible sleeve for gripping a catheter inserted in said longitudinal through hole of said flexible tubular sleeve; wherein
      transition from said non-gripping position to said gripping position is causable by said second portions of said arms frictioning transversely against said cantilevered structures and pushing said cantilevered structures towards one another.

11. The catheter connector device of claim 10, wherein the second portion of each arm is tapered.

12. The catheter connector device of claim 10, wherein said arms of said push-button further comprise respective third portions separated a second distance greater than said first distance, wherein, when said catheter connector device is in said non-gripping position, said third portions embrace said cantilevered structures.

13. The catheter connector device of claim 10, wherein one or more of said at least two arms comprises a lip configured to engage with a mating lip of said catheter connector main body when said catheter connector device is in said gripping position, preventing said push-button from moving outwardly from said gripping position to said non-gripping position.

14. The catheter connector device of claim 10, wherein said first port and said second port are arranged at opposite ends along a longitudinal direction of said catheter connector main body, and wherein said first hole, said tubular sleeve and said second hole are aligned along said longitudinal direction.

15. The catheter connector device of claim 10, wherein said push-button further comprises at least one limiting lip engageable with an internal surface of said catheter connector main body and preventing said push-button from being removed from said main body.

16. A catheter connector device for interfacing between a catheter and a fluid application and/or removal device, the catheter connector device comprising:
   a catheter connector main body delimiting an internal cavity, wherein a first port and a second port are formed on the catheter connector main body, said first and second ports comprising respective first and second holes communicating said internal cavity with an outside of said catheter connector main body;
   at least two flexible cantilevered structures extending from said catheter connector main body into said internal cavity;
   a flexible tubular sleeve arranged between said at least two cantilevered structures, said flexible sleeve comprising a longitudinal through hole in fluid communication with said first and second holes;
   a push-button, comprising a push-button body operable from outside said catheter connector main body, and at least two arms extending into the internal cavity, said arms arranged in a spaced-apart configuration, wherein first portions of said arms are separated a first distance, second portions of said arms are separated an increasing distance greater than said first distance, and third portions of said arms are separated a second distance greater than said first distance; wherein
   said catheter connector device is configured to adopt:
      a non-gripping position, in which said cantilevered structures are biased to separate from one another and occupy a width that is greater than said first distance, and in which said third portions embrace said cantilevered structures; and
      a gripping position in which said push-button is pushed inwardly towards said internal cavity, and said first portions of said arms embrace and retain said cantilevered structures in a deformed position in which said cantilevered structures apply a pressure against said flexible tubular sleeve and compress said flexible sleeve for gripping a catheter inserted in said longitudinal through hole of said flexible tubular sleeve; wherein
      transition from said non-gripping position to said gripping position is causable by said second portions of said arms frictioning transversely against said cantilevered structures and pushing said cantilevered structures towards one another.

17. The catheter connector device of claim 16, wherein the second portion of each arm is tapered.

18. The catheter connector device of claim 16, wherein one or more of said at least two arms comprises a lip configured to engage with a mating lip of said catheter connector main body when said catheter connector device is in said gripping position, preventing said push-button from moving outwardly from said gripping position to said non-gripping position.

19. The catheter connector device of claim 16, wherein said first port and said second port are arranged at opposite ends along a longitudinal direction of said catheter connector main body, and wherein said first hole, said tubular sleeve and said second hole are aligned along said longitudinal direction.

20. The catheter connector device of claim 16, wherein said push-button further comprises at least one limiting lip engageable with an internal surface of said catheter connector main body and preventing said push-button from being removed from said main body.

\* \* \* \* \*